United States Patent [19]

Edwards

[11] Patent Number: 4,605,657
[45] Date of Patent: Aug. 12, 1986

[54] 4-QUINAZALONE FUNGICIDES
[75] Inventor: Laroy H. Edwards, Napa, Calif.
[73] Assignee: Chevron Research Company, San Francisco, Calif.
[21] Appl. No.: 728,997
[22] Filed: Apr. 30, 1985
[51] Int. Cl.[4] .................. A61K 31/505; C07D 239/95; A01N 43/54
[52] U.S. Cl. .......................... 514/259; 71/3; 544/285
[58] Field of Search .......................... 544/285; 514/259

[56] References Cited
U.S. PATENT DOCUMENTS
4,039,508  8/1977  Dhami .................. 544/285

OTHER PUBLICATIONS
Bhargava, et al., "Indian J. Chem.", vol. 15B, No. 7, 1977, pp. 659–660.

Primary Examiner—Glennon H. Hollrah
Assistant Examiner—James H. Turnipseed
Attorney, Agent, or Firm—S. R. LaPaglia; T. G. DeJonghe; S. L. Biggs

[57] ABSTRACT

Compounds of the formula:

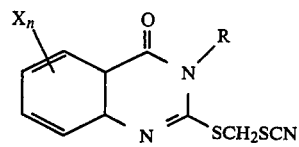

wherein X is independently halogen, lower alkyl of 1 to 6 carbon atoms, lower alkoxy of 1 to 6 carbon atoms, nitro, the group $R^1$—$S(O)_m$— wherein $R^1$ is lower alkyl of 1 to 6 carbon atoms and m is 0, 1 or 2, amino, or trifluoromethyl; n is 0, 1, 2 or 3; and R is alkyl of 1 to 10 carbon atoms; cycloalkyl of 3 to 8 carbon atoms; lower alkenyl of 2 to 6 carbon atoms; or lower alkynyl of 2 to 6 carbon atoms, all optionally substituted with 1 to 3 of the same or different halogen atoms, or aryl of 6 to 12 carbon atoms or substituted aryl substituted with 1 to 3 groups independently selected from lower alkyl of 1 to 4 carbon atoms, lower alkoxy of 1 to 4 carbon atoms, lower alkylthio of 1 to 4 carbon atoms, oxidized alkylthio, nitro, cyano, or halogen are fungicidal.

19 Claims, No Drawings

4-QUINAZALONE FUNGICIDES

BACKGROUND OF THE INVENTION

The present invention relates to novel 4-quinazalone compounds which are useful as fungicides.

Commonly-assigned U.S. patent application "Algicidal and Fungicidal 2-Haloalkyl-3-oxo-4-Substituted Quinazaline" discloses compounds of the formula:

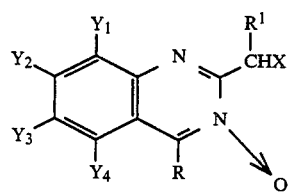

wherein R is hydrogen, lower alkyl, lower alkyl substituted with one to three of the same or different halogens, phenyl or phenyl substituted with 1 or 3 of the same or different substituents selected from a group consisting of lower alkyl, lower alkoxy, lower alkylthio, fluoro, chloro, bromo, iodo, nitro, cyano, or lower alkyl substituted with one to three of the same or different halogens, $R^1$ is hydrogen, lower alkyl, or lower alkyl substituted with one to three of the same or different halogens, $Y_1$, $Y_2$, $Y_3$ and $Y_4$ are independently selected from a group consisting of hydrogen, lower alkyl, lower alkoxy, lower alkylthio, fluoro, chloro, bromo, iodo, nitro, cyano, or lower alkyl substituted with one to three of the same or different halogens and X is fluoro, chloro, bromo, iodo, cyano, lower alkoxy, thiocyano, imidazolyl, and

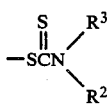

where $R^3$ and $R^2$ are the same or different lower alkyl, as fungicidal and algicidal.

SUMMARY OF THE INVENTION

The 4-quinazalone compounds of the present invention have the general formula:

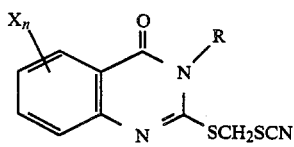

wherein X is independently halogen, lower alkyl of 1 to 6 carbon atoms, lower alkoxy of 1 to 6 carbon atoms, nitro, the group $R^1$—$S(O)_m$— wherein $R^1$ is loer alkyl of 1 to 6 carbon atoms and m is 0, 1 or 2; amino, or trifluoromethyl; n is 0, 1, 2 or 3; and R is alkyl of 1 to 10 carbon atoms; cycloalkyl of 3 to 8 carbon atoms; lower alkenyl of 2 to 6 carbon atoms; or lower alkynyl of 2 to 6 carbon atoms, all optionally substituted with 1 to 3 of the same or different halogen atoms, or aryl of 6 to 12 carbon atoms or substituted aryl substituted with 1 to 3 groups independently selected from lower alkyl of 1 to 4 carbon atoms, lower alkoxy of 1 to 4 carbon atoms, lower alkylthio of 1 to 4 carbon atoms, oxidized alkylthio, nitro, cyano, or halogen.

Among other factors, the present invention is based upon my finding that these compounds are surprisingly effective in controlling fungi, in particular certain plant fungal diseases, including downy mildews.

Preferred X groups include chlorine, nitro, trifluoromethyl and methyl.

Preferred R groups include phenyl and lower alkyl.

The preferred halogen is chlorine.

Definitions

As used herein, the following terms have the following meanings unless expressly stated to the contrary.

The term "alkyl" refers to both straight- and branched-chain alkyl groups. The term "lower alkyl" refers to both straight- and branched-chain alkyl groups having a total of from 1 to 6 carbon atoms and includes primary, secondary and ertiary alkyl groups. Typical lower alkyls include, for example, methyl, ethyl, n-propyl, isopropyl, n-butyl, isobutyl, t-butyl, n-pentyl, n-hexyl, and the like.

The term "cycloalkyl" refers to cyclic alkyl groups. The term "lower cycloalkyl" refers to groups having from 3 to 6 carbon atoms in the ring, and includes cyclopropyl, cyclobutyl, cyclopentyl, and cyclohexyl.

The term "alkylene" refers to the group —$(CH_2)_m$— wherein m is an integer greater than zero. Typical alkylene groups include, methylene, ethylene, propylene and the like.

The term "alkylthio" refers to the group 'S— wherein R' is alkyl. The term "lower alkylthio" refers to alkylthio groups having 1 to 6 carbon atoms; examples include methylthio, ethylthio, n-hexylthio, and the like.

The term "alkoxy" refers to the group —OR' wherein R' is an alkyl group. The term "lower alkoxy" refers to alkoxy groups having from 1 to 6 carbon atoms; examples include methoxy, ethoxy, n-hexoxy, n-propoxy, isopropoxy, isobutoxy, and the like.

The term "alkenyl" refers to unsaturated alkyl groups having a double bond [e.g., $CH_3CH=CH(CH_2)_2$] and includes both straight- and branched-chain alkenyl groups. "Lower alkenyl" refers to groups having a total of from 2 to 6 carbon atoms. Typical lower alkenyl groups include, for example, vinyl, propenyl, but-3-enyl, hex-4-enyl, 2-methyl-pent-4-enyl, and the like.

The term "halo" or "halogen" refers to the groups fluoro, chloro, bromo and iodo.

The term "haloalkenyl" refers to alkenyl groups substituted with from 1 to 3 halogen atoms. "Lower haloalkenyl" refers to groups having a total of from 2 to 6 carbon atoms, and includes, for example, 1-chloropropenyl, 2,3-dibromo-but-3-enyl, and the like.

The term "alkynyl" refers to unsaturated alkyl groups having a triple bond (e.g., $CH_3C\equiv CCH_2CH_2$—) and includes both straight- and branched-chain alkynyl groups. "Lower alkynyl" refers to groups having a total of from 2 to 6 carbon atoms. Typical lower alkynyl groups include propynyl, but-3-ynyl, hex-4-ynyl, 2-methyl-pent-4-ynyl, and the like.

The term "hydroxy alkyl" refers to the group —R'-'OH wherein R" is branched or unbranched alkylene and the hydroxy can be on a primary, secondary or a tertiary carbon. Examples include hydroxyethyl and 2-hydroxy-propyl and 2-hydroxy-2-methylbutyl.

The term "aryl" refers to aryl groups having from 6 to 12 carbon atoms and includes, for example, phenyl, p-chlorophenyl, m-methylphenyl, p-butylphenyl, m-trifluoromethylphenyl, naphthyl, and the like.

The term "aralkyl" refers to an alkyl group of 1 to 4 carbons substituted with an aryl group of from 6 to 12 carbons and includes, for example, benzyl, p-chlorobenzyl, p-methylbenzyl and 2-phenylethyl.

The term "alkylamino" refers to the group R'R"N— wherein R' is alkyl and R" is hydrogen or alkyl, the term "lower alkylamino" refers to alkylamino groups having 1 to 6 carbon atoms. Typical alkylamino groups include methylamino, ethylamino, diethylamino, dimethylamino, and the like.

Pests are any insect, rodent, nematode, fungus, weed, or any form of terrestrial or aquatic plant or animal life or virus, bacterial organism or other microorgniasm (except those viruses, bacteria or other microorganisms existing in living humans or other living animals) considered injurious to health, the environment or man's economic well-being.

DETAILED DESCRIPTION OF THE INVENTION

The compounds of the present invention may be conveniently prepared according to the following synthetic scheme:

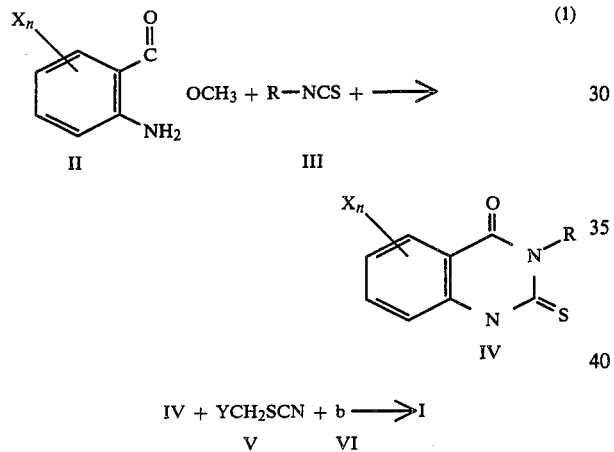

wherein X, n and R are as previously defined in conjunction with formula I, Y is halogen and b is a base.

Reaction (1) is conducted by combining approximately equimolar amounts of II and III in solvent. Optionally, an equivalent amount of a base such as triethylamine may be added as a catalyst. The reaction is conducted at a temperature of about 25° C. to about 100° C., preferably from about 80° C. to about 100° C. or at reflux and is generally complete within about 8 to about 24 hours. The product, IV, is isolated by conventional procedures such as stripping, extraction, precipitation, filtration, chromatography, and the like.

Reaction (2) is conducted by combining approximately equimolar amounts of IV, V and VI in solvent. (It may be preferable to use a slight excess of V and VI relative to IV, on the order of about 1 to about 1.1 equivalents V per equivalent IV and about 1 to about 2 equivalents VI per equivalent IV. Although the reactants may be combined in any order, it may be preferable to first add VI and IV in solvent, allow the mixture to react to form the salt and then add V in solvent. The reaction is conducted at a temperature of about 25° C. to about 80° C., preferably from at reflux and is generally complete within about 6 to about 12 hours. The product, I, is isolated by conventional procedures such as stripping, extraction, crystallization, filtration, precipitation, chromatography and the like. Suitable solvents include polar organic solvents, such as ethanol, dimethoxy ethane, dimethylformamide and dimethylsulfoxide.

Utility

These compounds are active as fungicides and are particularly effective in controlling a variety of fungi which are deleterious to plants, including plant fungal infections. Some of these compounds are useful in controlling leaf blights caused by organisms such as *Phytophthora infestans, Septoria apii, Alternaria solani conidia,* and powdery mildews such as that caused by *Erysiphe polygoni.* However, some of the compounds of this invention may be more fungicidally active than others against particular fungi.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus, and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersants. These compositions normally contain from about 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols and polyvinyl alcohols,; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant-growth regulators, fertilizers, etc.

A further understanding of the invention can be had in the following non-limiting Examples. Wherein, unless expressly stated to the contrary, all temperature ranges refer to the Centigrade system and the term "ambient" or "room temperature" refers to about 20° C. to about 25° C. The term "percent" refers to gram moles. The term "equivalent" refers to a quantity of reagent equal in moles, to the moles of the preceding or succeeding reagent recited in that examples in terms of finite moles or finite weight or volume. Also, unless expressly stated to the contrary, geometric isomer and racemic mixtures are used as starting materials and correspondingly, isomer mixtures are obtained as products.

EXAMPLES

EXAMPLE 1

Preparation of 2-mercapto-3-phenyl-4(3H)-quinazolinone

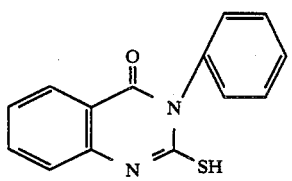

In a 500 ml, three-neck round bottom flask equipped with magnetic stirrer, 25 g (0.17 moles) methyl anthranilate in 100 ml methylene chloride was placed. Into that mixture 23.0 g (0.17 moles) phenyl isothiocyanate in 50 ml methylene chloride was dropped in. The reaction mixture was stirred overnight at ambient temperature. The reaction mixture was refluxed at 40° C. for one hour. Ether (about 50 ml) was added; a precipitate formed which was removed by suction filtration to give the above-identified product.

EXAMPLE 2

Preparation of 2-Thiocyanomethylthio-3-phenyl-4(3H)-quinazoline

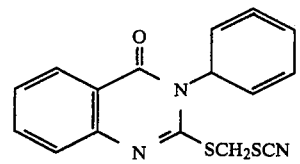

In a 500 ml, 3-neck round bottom flask equipped with a magnetic stirrer, 20 g (0.08 moles) 2-mercapto-3-phenyl-4(3H)-quinazolinone (the product of Example 1) in 200 ml ethanol was placed. To that mixture, 5.5 g (0.04 mole) potassium carbonate was added; the resulting mixture was refluxed at about 45° C. for 5 hours. Then, 8.6 g (0.08 moles) chloromethyl thiocyanate in 25 ml methylene chloride was dropped in; the resulting mixture was stirred overnight. The reaction mixture was refluxed for 45° C. and then allowed to stir at ambient temperature overnight. The mixture was suction filtered; the liquid was stripped. The solid and liquid was combined, washed with water, extracted with methylene chloride, dried and stripped to give a brownish oil, in which crystals formed upon standing. Ether was added and the resulting mixture was stirred over the weekend. The crystalline product was recovered by suction filtration, yielding the product as a white solid, melting point 130°–134° C.

Elemental analysis for $C_{16}H_{11}N_3OS_2$ showed: calculated % C 59.05, % H 3.41, and % N 12.91; found % C 59.02, % H 4.02, and % N 13.49.

EXAMPLE 3

Preparation of 1-[2-(methoxycarboxyl)phenyl]-3-methylthiourea

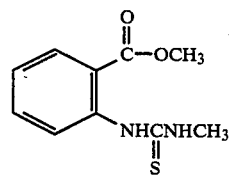

To a stirred solution of 50 g (0.3 moles) methyl anthranilate in 200 ml methylene chloride, 21.9 g (0.3 moles) methyl isothiocyante in 50 ml methylene chloride was added dropwise. The reaction mixture was stirred overnight at ambient temperature, refluxed at 40° C. for 4½ hours, and stirred overnight. The reaction mixture was stripped to give the above-identified product.

EXAMPLE 4

Preparation of
2-Thiocyanomethylthio-3-methyl-4(3H)-quinazolinone

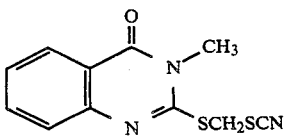

To a stirred solution (mixture) of 32.05 g (0.14 mole) 1-[2-(methoxycarboxyl)phenyl]-3-methyl thiourea (the product of Example 3) in 200 ml ethanol, 9.6 g (0.14 mole) potassium carbonate was added. The resulting mixture was refluxed 1½ hours then allowed to stir overnight, and refluxed at 45° C. for 4 hours. To that mixture 15 g (0.14 mole) chloromethyl thiocyanate in 25 ml ethanol was added dropwise. The reaction mixture was refluxed at 45° C. for 2.5 hours, stirred at ambient temperature overnight, and refluxed at 45° C. for about 2 hours. The reaction mixture was cooled and the inorganic salts were removed by filtration. The liquid was stripped. Ether was added to the residue to give a precipitate, the above-identified product as a solid, melting point 118°–121° C.

Elemental analysis for $C_{11}H_9N_3OS_2$ showed: calculated % C 50.17, % H 3.44, and % N 15.96; found % C 52.36; % H 3.82, and % N 15.73.

EXAMPLE 5

Preparation of 2-mercapto-3-allyl-4(3H)-quinazolinone

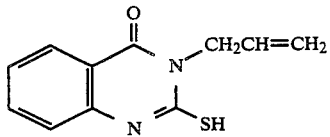

To a stirred mixture of 50 g (0.33 mole) methyl anthranilate in 100 ml methylene chloride, 32.7 g (0.33 mole) allyl isothiocyanate in 50 ml methylene chloride was added dropwise. The reaction mixture was refluxed at 40° C. one hour, stirred over the weekend at ambient temperature, and refluxed at 40° C. for one hour. The reaction mixture was stripped. Additional methylene chloride (200 ml) was added; the resulting mixture was refluxed at 40° C. for 7 hours, and then stirred about 1½ days at ambient temperature. The reaction mixture was stripped. Ether was added; a precipitate formed. The above-identified product was isolated by suction filtration.

EXAMPLE 6

Preparation of
2-Thiocyanomethyl-3-allyl-4(3H)-quinazolinone

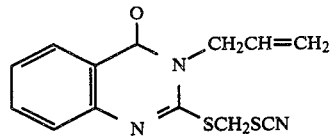

To a mixture of 5.8 g (0.03 mole) 2-mercapto-3-allyl-4(3H)-quinazolinone (the product of Example 5) in 200 ml dimethoxyethane, 5.4 g (0.05 mole) chloromethyl thiocyanate and 2.4 g (0.05 mole) 50% sodium hydride were added. The resulting mixture was stirred overnight at ambient temperature, refluxed at 50° C. for 8 hours, stirred overnight, refluxed at 50° C. for 8 hours and stirred overnight. The reaction mixture was washed with water, extracted with methylene chloride, dried over magnesium sulfate and stripped. The oily residue was triturated with ether, to give the above-identified product, as a solid, melting point 73°–76° C.

Elemental analysis for $C_{13}H_{11}N_3OS_2$ showed: calculated % C 53.96, % H 3.83, and % N 14.52; found % C 52.62, % H 4.02, and % N 14.72.

Compounds made in accordance with the methods disclosed in the Detailed Description of the Invention and with Examples 1 to 6 are found in Table I.

In addition, by following the procedures disclosed in the Detailed Description of the Invention and Examples 1 to 6 and using the appropriate starting materials and reagents, the following compounds are made:

2-thiocyanomethyl-3-phenyl-6-trifluoromethyl-4(3H)-quinazolinone;
2-thiocyanomethyl-3-phenyl-7-trifluoromethyl-4(3H)-quinazolinone;
2-thiocyanomethyl-3-phenyl-7-chloro-4(3H)-quinazolinone;
2-thiocyanomethyl-3-phenyl-6-methylsulfonyl-4(3H)-quinazolinone;
2-thiocyanomethyl-3-phenyl-7-methylsulfonyl-4(3H)-quinazolinone;
2-thiocyanomethyl-3-n-butyl-6-chloro-4(3H)-quinazolinone;
2-thiocyanomethyl-3-n-butyl-7-chloro-4(3H)-quinazolinone;
2-thiocyanomethyl-3-n-butyl-6-trifluoromethyl-4(3H)-quinazolinone;
2-thiocyanomethyl-3-n-butyl-7-trifluoromethyl-4(3H)-quinazolinone;
2-thiocyanomethyl-3-n-butyl-6-methylsulfonyl-4(3H)-quinazolinone;
2-thiocyanomethyl-3-n-butyl-7-methylsulfonyl-4(3H)-quinazolinone;
2-thiocyanomethyl-3-cyclohexyl-6-chloro-4(3H)-quinazolinone;
2-thiocyanomethyl-3-cyclohexyl-7-chloro-4(3H)-quinazolinone;
2-thiocyanomethyl-3-cyclohexyl-6-trifluoromethyl-4(3H)-quinazolinone;
2-thiocyanomethyl-3-cyclohexyl-7-trifluoromethyl-4(3H)-quinazolinone;
2-thiocyanomethyl-3-cyclohexyl-6-methylsulfonyl-4(3H)-quinazolinone;
2-thiocyanomethyl-3-cyclohexyl-7-methylsulfonyl-4(3H)-quinazolinone;
2-thiocyanomethyl-3-methyl-6-chloro-4(3H)-quinazolinone;
2-thiocyanomethyl-3-methyl-7-chloro-4(3H)-quinazolinone;
2-thiocyanomethyl-3-methyl-6-trifluoromethyl-4(3H)-quinazolinone;
2-thiocyanomethyl-3-methyl-7-trifluoromethyl-4(3H)-quinazolinone;
2-thiocyanomethyl-3-methyl-6-methylsulfonyl-4(3H)-quinazolinone; and
2-thiocyanomethyl-3-methyl-7-methylsulfonyl-4(3H)-quinazolinone.

EXAMPLE A

Mycelial Inhibition

Compounds were evaluated for in vitro fungicidal effectiveness by means of a mycelial inhibition test. This test is designed to measure the fungitoxic activity of fungicidal chemicals in terms of their degree of inhibition of mycelium growth. Fungi used were *Pythium ultimum, Rhizoctonia solani, Fusarium moniloforme, Botrytis cinerea, Aspergillus niger* and *Ustilago hordeii.* Each compound to be tested was dissolved in acetone to 500 ppm concentration. Paper strips were infused with the particular mycelium growth by covering the paper with a potato dextrose broth culture of mycelial suspension. The papers were then placed on potato dextrose agar plates and sprayed by means of a micro sprayer with the fungicidal solution. The treated paper strips were incubated at 25° C. and the data is taken after 24 hours. Fungicidal activities are measured by a zone of inhibited mycelial growth from the center of the paper strip in terms of $mg/cm^2$ needed for 99% control of the fungus ($ED_{99}$). The effectiveness of the compounds for fungicidal activity are reported in Table II in terms of the percent of the $ED_{99}$ of the test compound of the $ED_{99}$ of the standard Difolatan ®.

EXAMPLE B

Tomato Late Blight

Compounds were tested for the preventative control of the Tomato Late Blight organism *Phytophthora infestans.* Five- to six-week old tomato (cultivar Bonny Best) seedlings were used. The tomato plants were sprayed with a 200-ppm suspension of the test compound in acetone, water and a nonionic emulsifier. The sprayed plants were then inoculated 1 day later with the organism, placed in an environmental chamber and incubated at 66° F. to 68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table II.

EXAMPLE C

Rice Blast

Compounds of this invention were tested for control of the Rice Blast organism *Piricularia oryzae*, using 10-to 14-day old rice plant seedlings (Calrose M-9 variety). Seedling plants were sprayed with a 625-ppm solution of the test compound in acetone, water and a nonionic emulsifier (ORTHO X-77 spreader). The sprayed plants were inoculated 1 day later with the orgnaism in an environmental chamber. After inoculation, the plants were kept in an environmental chamber for about 48 hours under conditions of about 72° F. to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on the untreated check plants:

$$\% \text{ Control} = 100 - 100 \times \left( \frac{\% \text{ disease in treated plants}}{\% \text{ disease in check}} \right)$$

The results are tabulated in Table II.

EXAMPLE D

Tomato Early Blight

Compounds were tested for the control of the Tomato Early Blight organism *Alternaria solani conidia.* Tomato (variety Bonny Best) seedlings of 6 to 7 weeks old were used. The tomato plants were sprayed with a 200-ppm solution of the test compound in an acetone-and-waer solution containing a small amount of a nonionic emulsifier. The sprayed plants were inoculated 1 day later with the organism, placed in the environment chamber and incubated at 66° F. to 68° F. and 100% relative humidity for 24 hours. Following the incubation, the plants were maintained in a greenhouse for about 12 days. Percent disease control was based on the percent disease development on untreated check plants. The results are tabulated in Table II.

EXAMPLE E

Celery Late Blight

The Celery Late Blight tests were conducted using celery (Utah) plants 11 weeks old. The Celery Late Blight organism was *Septoria apii.* The celery plants were sprayed with 200-ppm solutions of the candidate toxicant mixed with acetone, water and a nonionic emulsifier. The plants were then inoculated with the organism and placed in an environmental chamber and incubated at 66° F. to 68° F. in 100% reltive humidity for an extended period of time (approximately 48 hours). Following the incubation, the plants were allowed to dry and then were maintained in a greenhouse for approximately 14 days. The percent disease control provided by a given test compound is based on the percent disease reduction relative to untreated check plants. The results are reported in Table II.

EXAMPLE F

Bean Powdery Mildew

Compounds were tested for the control of the Bean Powdery Mildew organiasm *Erysiphe polygoni.* Seedling bean plants were sprayed with a 250-ppm solution of the test compound in acetone, water and a nonionic emulsifier. The sprayed plants were then inoculated 1 day later with the orgniasm. The plants were maintained for 10 days at temperatures of 68/° F. at night with daytime temperatures of 72° F. to 80° F.: relative humidity was maintained at 40% to 60%. The percent disease control provided by a given test compound was based on the percent disease reduction relative to the untreated check plants. The results as percent control are tabulated in Table II.

EXAMPLE G

Bean Rust

Compounds were evaluated for their ability to eradicate Bean Rust caused by *Uromyces phaseoli typica* on pinto beans.

Pinto bean plants, variety Idaho 1-11, 16 (summer) or 19 (winter) days old were inoculated with a 50-ppm suspension of uredospores in waer containing a small amount of nonionic surfactant. The inoculated plants were placed in an environmental chamber immediately after inoculation and incubated 20 hours. Following the incubation period, the plants were removed from the chamber and placed in a greenhouse maintained at 66°–68° F. and 60–80% relative humidity. Two days after inoculation, the plants were treated by spraying with a 200-ppm solution of test compound in an acetone and water carrier formulation containing a small amount of nonionic surfactant. One or two replicate pots (each containing two plants) were used for each compound. In addition one or two replicate pots were sprayed with the same carrier formulation (without a test compound) as a control (hereinafter "untreated Checks"). The plants were kept in the greenhouse until evaluated. The plants were evaluated for disease control when disease symptoms were well developed on the untreated Checks, normally about 14 days after treatment. The percentage disease control (or eradication) procided by a test compound was based on the percent disease reduction relative to the untreated Checks. The results are reported in Table II.

TABLE I

Compounds of the formula:

$$X\text{-}C_6H_3(\text{-}CH_2\text{-}NR\text{-})(\text{-}N=C\text{-}SCH_2SCN)$$

| Compound No. | | R | X | Physical State | %C Calc. | %C Found | %H Calc. | %H Found | %N Calc. | %N Found |
|---|---|---|---|---|---|---|---|---|---|---|
| 1 | 44130 | —CH₃ | —H | Tan solid, mp 118–121° C. | 50.17 | 52.36 | 3.44 | 3.82 | 15.96 | 15.73 |
| 2 | 45299 | —CH(CH₃)₂ | —H | Yellow solid, mp 77–79° C. | 53.5 | 48.86 | 4.4 | 3.25 | — | — |
| 3 | 45179 | —(CH₂)₂CH₃ | —H | White solid, mp 114–117° C. | 53.58 | 52.66 | 4.50 | 4.59 | 14.42 | 14.22 |
| 4 | 45178 | —(CH₂)₃CH₃ | —H | White solid, mp 86–90° C. | 55.05 | 57.86 | 4.95 | 5.4 | 13.76 | 12.63 |
| 5 | 45092 | tetrahydrothiopyranyl | —H | Off-white solid, mp 110–113° C. | 57.98 | 58.94 | 5.17 | 5.25 | 12.68 | 12.48 |
| 6 | 44318 | —CH₂CH=CH₂ | —H | Solid, mp 73–76° C. | 53.96 | 52.62 | 3.83 | 4.02 | 14.52 | 14.72 |
| 7 | 44083 | phenyl | —H | tan solid, mp 130–134° C. | 59.05 | 59.02 | 3.41 | 4.02 | 12.91 | 13.49 |
| 8 | 45821 | phenyl | —Cl | White solid mp 168–170° C. | 53.41 | 49.82 | 2.81 | 2.77 | 11.40 | 11.64 |
| 9 | 45187 | 2-methoxyphenyl | —H | White solid, mp 164–167° C. | 57.44 | 57.29 | 3.69 | 4.02 | 11.82 | 11.33 |
| 10 | 45187 | 4-methoxyphenyl | —H | White solid, mp 164–167° C. | 57.44 | 57.03 | 3.69 | 3.64 | 11.82 | 11.74 |
| 11 | 44293 | 3,4-dichlorophenyl | —H | solid, mp 160–163° C. | 48.74 | 51.31 | 2.3 | 2.58 | 10.66 | 11.16 |

TABLE I-continued

Compounds of the formula:

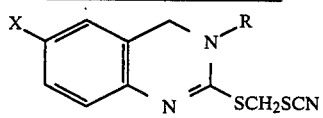

| Compound No. | R | X | Physical State | ELEMENTAL ANALYSIS | | | | | |
|---|---|---|---|---|---|---|---|---|---|
| | | | | % C | | % H | | % N | |
| | | | | Calc. | Found | Calc. | Found | Calc. | Found |
| 12  44243 | 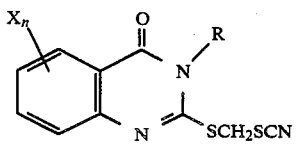 | —H | White solid, mp 117–119° C. | 48.74 | 48.79 | 2.30 | 2.44 | 10.66 | 10.24 |

TABLE II

FUNGICIDAL ACTIVITY

| Compound | Pyth. | Rhiz. | Fusar. | Botry. | Asper. | Ustil. | TLB | RB | TEB | CLB | BPM | BR |
|---|---|---|---|---|---|---|---|---|---|---|---|---|
| 1  44130 | 0 | 25 | 0 | 0 | 20 | 0 | 94 | 66 | 0 | 33 | 0 | 0 |
| 2  45299 | 0 | 0 | 0 | 0 | 0 | 0 | 31 | 0 | — | 97 | 94 | 0 |
| 3  45179 | 0 | 0 | 0 | 0 | 0 | 0 | 63 | 0 | 0 | 25 | 0 | 0 |
| 4  45178 | 0 | 0 | 0 | 0 | 0 | 0 | 56 | 69 | 0 | 89 | 94 | 0 |
| 5  45092 | 0 | 0 | 0 | 0 | 0 | 0 | 86 | 30 | 0 | 10 | 95 | 0 |
| 6  44318 | 0 | 28 | 0 | 0 | 0 | 18 | 59 | 56 | 0 | 10 | 0 | 0 |
| 7  44083 | 0 | 0 | 0 | 0 | 0 | 0 | 92 | — | 0 | 60 | 0 | 0 |
| 8  45821 | 88 | 83 | 0 | 24 | 41 | 34 | 47 | — | 13 | 97 | 0 | 0 |
| 9  45187 | 0 | 0 | 0 | 0 | 0 | 0 | 66 | 0 | — | 72 | 12 | 0 |
| 10  45093 | 0 | 0 | 0 | 0 | 0 | 0 | 6 | 20 | 0 | 0 | 0 | 0 |
| 11  44293 | 0 | 40 | 0 | 0 | 0 | 0 | 61 | 56 | 0 | 75 | 0 | 0 |
| 12  44243 | 0 | 0 | 0 | 0 | 0 | 0 | 0 | 0 | 50 | 33 | 0 | 0 |

Pyth. = *Pythium ultimum*
Rhiz. = *Rhizoctonia solani*
Fusar. = *Fusarium moniloforme*
Botry. = *Botyrtis cinerea*
Asper. = *Aspergillus niger*
Ustil. = *Ustilago hordeii*
TLB = Tomato Late Blight
RB = Rice Blast
TEB = Tomato Early Blight
CLB = Celery Late Blight
BPM = Bean Powdery Mildew
BR = Bean Rust

What is claimed is:

1. A compound of the formula:

wherein X is independently halogen, lower alkyl of 1 to 6 carbon atoms, lower alkoxy of 1 to 6 carbon atoms, nitro, the group $R^1$—$S(O)_m$— wherein $R^1$ is lower alkyl of 1 to 6 carbon atoms and m is 0, 1 or 2, amino or trifluoro methyl; n is 0, 1, 2 or 3; and R is alkyl of 1 to 10 carbon atoms, cycloalkyl of 3 to 8 carbon atoms, lower alkenyl of 2 to 6 carbon atoms or lower alkynyl of 2 to 6 carbon atoms, all optionally substituted with 1 to 3 of the same or different halogen atoms; aryl of 6 to 12 carbon atoms or substituted aryl substituted with 1 to 3 substituents, independently selected from lower alkyl of 1 to 4 carbon atoms, lower alkoxy of 1 to 4 carbon atoms, lower alkyl thio of 1 to 4 carbon atoms, lower alkylsulfinyl of 1 to 4 carbon atoms, lower alkyl sulfonyl of 1 to 4 carbon atoms, nitro, cyano or halogen.

2. A compound according to claim 1 wherein n is 0 or 1 and X is halogen.

3. A compound according to claim 2 wherein R is aryl or substituted aryl.

4. A compound according to claim 3 wherein R is phenyl.

5. A compound according to claim 4 wherein X is chlorine.

6. A compound according to claim 5 wherein n is 0.

7. A compound according to claim 5 wherein n is 1.

8. A method of controlling fungi which comprises contacting said fungi or their growth environment with a fungicidally effective amount of a compound of claim 1.

9. A method of controlling fungi which comprises contacting said fungi or their growth environment with a fungicidally effective amount of a compound of claim 2.

10. A method of controlling fungi which comprises contacting said fungi or their growth environment with a fungicidally effective amount of a compound of claim 4.

11. A method of controlling fungi which comprises contacting said fungi or their growth environment with a fungicidally effective amount of a compound of claim 5.

12. A method of controlling fungi which comprises contacting said fungi or their growth environment with a fungicidally effective amount of a compound of claim 6.

13. A method of controlling fungi which comprises contacting said fungi or their growth environment with a fungicidally effective amount of a compound of claim 7.

14. A fungicidal composition which comprises a biologically inert carrier and a fungicidally effective amount of a compound of claim 1.

15. A fungicidal composition which comprises a biologically inert carrier and a fungicidally effective amount of a compound of claim 2.

16. A fungicidal composition which comprises a biologically inert carrier and a fungicidally effective amount of a compound of claim 4.

17. A fungicidal composition which comprises a biologically inert carrier and a fungicidally effective amount of a compound of claim 5.

18. A fungicidal composition which comprises a biologically inert carrier and a fungicidally effective amount of a compound of claim 6.

19. A fungicidal composition which comprises a biologically inert carrier and a fungicidally effective amount of a compound of claim 7.

* * * * *